United States Patent
Chapman

(10) Patent No.: US 6,913,020 B2
(45) Date of Patent: Jul. 5, 2005

(54) RESTRAINT STORAGE, TRANSPORT, AND RAPID DEPLOYMENT APPARATUS AND METHOD

(75) Inventor: Bruce Chapman, Gardiner, NY (US)

(73) Assignee: Handle With Care, Inc., Gardiner, NY (US)

( * ) Notice: Subject to any disclaimer, the term of this patent is extended or adjusted under 35 U.S.C. 154(b) by 242 days.

(21) Appl. No.: 10/266,076

(22) Filed: Oct. 7, 2002

(65) Prior Publication Data

US 2003/0121524 A1 Jul. 3, 2003

Related U.S. Application Data

(60) Provisional application No. 60/327,619, filed on Oct. 6, 2001.

(51) Int. Cl.[7] ................................................. A61F 5/37
(52) U.S. Cl. ...................... 128/870; 128/882; 128/878; 128/879; 70/16; 224/914
(58) Field of Search .................................. 128/870, 882, 128/869, 876, 878, 879; 70/15, 16, 17, 18; 2/312, 315, 316, 317, 318, 322, 338; 224/914; D3/230, 226

(56) References Cited

U.S. PATENT DOCUMENTS

| | | | | |
|---|---|---|---|---|
| 3,143,262 A | * | 8/1964 | Sullivan ..................... 224/914 |
| 3,826,414 A | * | 7/1974 | Valadez ..................... 224/914 |
| 3,870,208 A | * | 3/1975 | Theodore ................... 224/914 |
| 4,741,051 A | * | 5/1988 | Bible ............................ 70/16 |
| 4,852,784 A | * | 8/1989 | Burton, Jr. ................. 224/914 |
| D338,106 S | * | 8/1993 | Elam .......................... D3/226 |
| D364,038 S | * | 11/1995 | Stanchin ..................... D3/230 |
| 5,511,706 A | * | 4/1996 | Hendrickson ............... 224/914 |
| 5,551,447 A | * | 9/1996 | Hoffman et al. ............ 128/869 |
| 5,562,238 A | * | 10/1996 | White ......................... 224/914 |
| 5,918,786 A | * | 7/1999 | Wise .......................... 224/914 |

\* cited by examiner

Primary Examiner—Fadi H. Dahbour
(74) Attorney, Agent, or Firm—Edward Etkin, Esq.

(57) ABSTRACT

An apparatus, and method of use thereof, for storing, transporting and deploying multiple restraint system components is provided. The inventive apparatus consists of two trays composed of flexible materials. The first tray is configured for storing wrist and ankle restraint systems, the second tray, smaller than the first tray, includes a top-mounted compartment for storing a multi-point restraint connection system. The storage compartment of second tray is secured to the tray by releasable connectors, and is at least partially disengaged to receive the various components of the multi-point restraint connection system, and releasably secured thereafter. The connection system is stored in such a manner as to partially display a portion of each system component outside of the storage compartment, with each portion oriented toward its eventual deployment area once the second tray is placed on the structure on which the EDP will be restrained. An optional secondary compartment may be provided on top of the storage compartment for storing a supplemental restraint system, such as the articulated upper body protection system. To complete the storage/transport configuration, the second tray is placed over a longitudinally folded first tray and the two trays are rolled up from one side to another. A releasable closure device secures the apparatus in its rolled up position. Advantageously, the storage configuration of the inventive apparatus enables easy and intuitive deployment thereof.

11 Claims, 6 Drawing Sheets

RESTRAINT STORAGE, TRANSPORT, AND RAPID DEPLOYMENT APPARATUS AND METHOD

REFERENCE TO PREVIOUSLY FILED APPLICATIONS

The present patent application claims priority from a previously filed commonly assigned U.S. Provisional Patent Application Ser. No.: 60/327,619, entitled "Multi-Point Soft Restraint Storage, Transport, and Rapid Deployment Apparatus and Method" filed on Oct. 6, 2001.

BACKGROUND OF THE INVENTION

The present invention is directed to an apparatus and method for storing, transporting, and deploying a multi-point soft mechanical restraint system and other restraint components that may be easily and quickly applied by a first person on a subject being held in a restrained position by a second person.

There are many thousands of human service and law enforcement agencies and facilities that provide care and supervision to aggressive, suicidal, and emotionally disturbed persons (hereinafter commonly referred to as "EDPs"). The staff and officers working in these agencies regularly come into physical contact with the EDPs through the use of physical subduing or restraint holds when the EDP becomes aggressive. Although there are many types of well-known physical subduing holds, the safest and most advantageous physical subduing hold is a Primary Restraint Technique (PRT) described in greater detail in a commonly assigned U.S. Pat. No. 6,273,091 entitled "Apparatus and Method for Safely Maintaining a Restraining Hold on a Person".

While restraint holds are useful for relatively short periods of time, often restraint of the EDP is necessary for an extended period of time. In such cases, the EDP must be restrained using some sort of a mechanical restraint system. Typically, this involves placing wrist and ankle restraints on the EDP so that the EDP may be restrained for an extended period of time at the place of the restraint hold, or, transported to another location while wearing the restraints. Also, for extended restraints, special beds with integrated restraints are used in many facilities. Previously known restraint systems involve mechanical locks—for example, the popular Posey TAT restraint utilizes a mechanical spring-loaded lock that require a special key to open. It takes at least 4–5 staff members to successfully apply such restraints at a speed of no lower than 2–3 minutes per restraint. During application of the restraints, the EDP must be held down and poses a constant threat to the staff members until the restraining process is complete. Furthermore, removal of such restraints in emergency situations (i.e., in a medical emergency) takes a significant amount of time since a key must be located and used to open each restraint on each limb—this is especially problematic because without the key, which may not be immediately available in case of an emergency, the restraints cannot be removed at all. Manipulation of the restraints once attached is difficult as well requiring several people to pull webbing through a complex system of buckles and connectors. Another problem that often arises, is that a bed with integrated mechanical restrains for restraining the EDP for extended periods of time may not be available when necessary, thus forcing the staff members to find alternate long-term restraint means.

Yet another disadvantage of previously known mechanical restraint systems is that by only restraining the EDP's arms and legs they still enable the EDP to struggle and potentially hurt themselves.

Finally, complex previously known restraint systems are expensive, heavy, and require extensive training to use properly. This is especially true of beds with integrated restraint systems.

The commonly assigned co-pending U.S. patent applications entitled "Soft Circular Restraint Apparatus and Method", "Rapid Deployment Soft Restraint Apparatus and Method", "Multi-Point Soft Restraint Apparatus and Method" and the commonly assigned co-pending U.S. provisional patent application entitled "Articulated Upper Body Protector Restraint Apparatus and Method", advantageously solve all of the above problems, and are all hereby incorporated by reference in its entirety. However, because the various inventive restraint systems have many individual components, there is some challenge in storing, transporting and deploying them correctly.

Thus, it would be desirable to provide an apparatus and method for quickly and easily deploying a mechanical restraint system, along with a multi-point restraint securing system and optional upper body protection system, for securing a restrained subject to a stationary or mobile structure. It would further be desirable to provide an apparatus and method for easily transporting and storing the mechanical restraint system along with the multi-point restraint securing system and other optional restraint components.

SUMMARY OF THE INVENTION

The apparatus of the present invention, and method of use thereof, remedies the problems associated with transporting and deploying various mechanical restraint systems that can be used to restraint violent and/or struggling EDPs. In brief summary, the inventive restraint storage, transport and rapid deployment apparatus advantageously provides: (1) compact and easy storage and transportation of various mechanical restraint systems; (2) novel construction enabling intuitive and quick deployment of restraint system components therefrom; and (3) lightweight and simple construction, making the inventive apparatus inexpensive to manufacture.

In summary, the inventive apparatus consists of two trays composed of flexible materials. The first tray is configured for storing wrist and ankle restraint systems as well as any other miscellaneous singular restraint system components (such as alternate wrist/ankle interconnects), the second tray, smaller than the first tray, includes a top-mounted compartment for storing a multi-point restraint connection system that is utilized to releasably connect the wrist and ankle restraint systems to a stationary or mobile structure (such as a bed or a wheelchair). In use for storage and transport, once the wrist and ankle restraint systems are releasably attached to the first tray, a potion of the first tray is folded over the wrist restraint system. Any optional additional restraint component is longitudinally positioned in the center of the folded tray. The storage compartment of second tray is secured to the tray by releasable connectors, and is at least partially disengaged to receive the various components of the multi-point restraint connection system, and releasably secured thereafter. The connection system is stored in such a manner as to partially display a portion of each system component outside of the storage compartment, with each portion oriented toward its eventual deployment area once the second tray is placed on the structure on which the EDP will be restrained. An optional secondary compartment may be provided on top of the storage compartment for storing a supplemental restraint system, such as the articulated upper body protection system To complete the storage/transport configuration, the second tray is placed over the folded first tray and the two trays are rolled up from one side to another. A releasable closure device secures the apparatus in its rolled up position. Advantageously, the storage configuration of the inventive apparatus enables easy and intuitive deployment thereof.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote corresponding or similar elements throughout the various figures.

DESCRIPTION OF THE PREFERRED EMBODIMENTS

Figure 1:
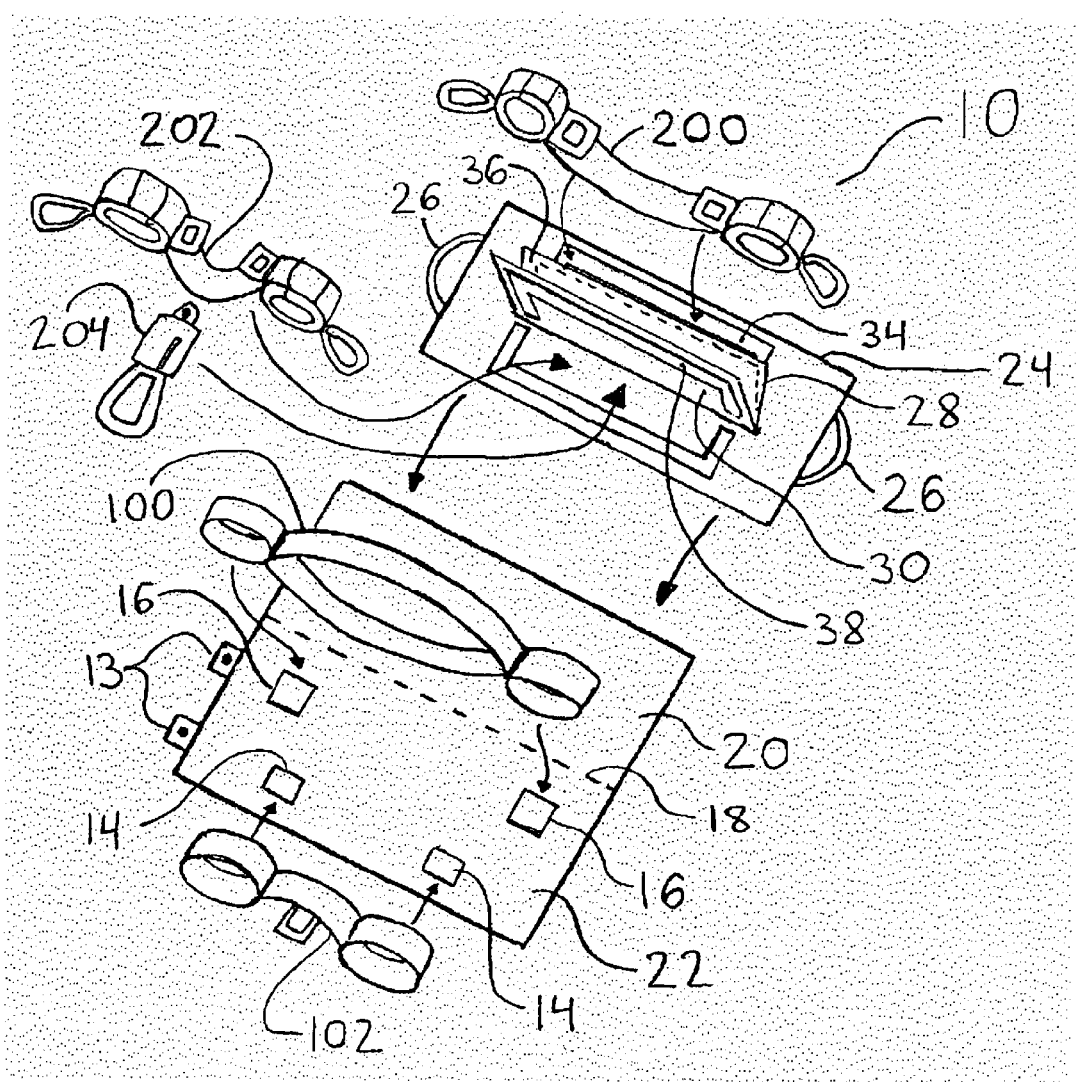
FIG. 1 shows an exploded isometric top view of the inventive restraint transport and deployment apparatus showing the lower tray for storing wrist and ankle restraints and an upper tray for storing a multi-point restraint connector system, all in open post-deployment positions.

The present invention relates to an apparatus and method for readily storing, transporting, and rapidly deploying multiple mechanical restraint system components, including but not limited to wrist and ankle restraint systems and a multi-point connector system that may be utilized to easily and quickly restrain a subject and then secure the subject in an ordinary bed or any other stationary or mobile structure. Preferably, the apparatus and method of the present invention are utilized in conjunction with soft circular restraints, interconnects the and multi-point restraint connection system such as those disclosed in the above-incorporated patent applications entitled, respectively, "Soft Circular Restraint Apparatus and Method" (hereinafter "R1"), "Rapid Deployment Soft Restraint Apparatus and Method" (hereinafter "R2"), and "Multi-Point Soft Restraint Apparatus and Method" (hereinafter "R3"). However, the inventive restraint storage, transport, and deployment apparatus (hereinafter "RSTD system") may be utilized with any other point connector and other mechanical restraint systems without departing from the spirit of the invention.

It should be understood that while the present invention refers to Emotionally Disturbed Persons (hereinafter "EDPs") and Staff Members, the inventive techniques and apparatus may be applied in virtually any situation where a subject is being restrained and application of mechanical restraints is warranted. Thus, the present invention is applicable in law enforcement, hospitals, mental health care facilities, drug and alcohol rehabilitation centers, etc.

Furthermore, while description of the various embodiments of the present invention refers to connecting to, and deploying onto, a bed, it should be understood that the inventive point connector elements may be advantageously deployed from the inventive RSTD system to connect to any stationary or mobile structure where it is desirable to maintain the EDP in a restrained position for an extended period of time.

Finally, while a number of exemplary releasable connectors are illustrated in the various drawings, it should be understood that other types of releasable connectors may be used as a matter of design choice without departing from the spirit of the invention.

Before application of any sort of mechanical restraints, it is important that control over the EDP is established by placing the EDP into a restraining hold. The Primary Restraint Technique (hereinafter "PRT") is an advantageous modular single person restraint that is applied by an EDP care professional (hereinafter "staff member") to an EDP from behind. The maneuvers involved in implementing the PRT are described in greater detail in connection with the Primary Restraint Technique (PRT) described in greater detail in a commonly assigned U.S. Pat. No. 6,273,091 entitled "Apparatus and Method for Safely Maintaining a Restraining Hold on a Person" which is hereby incorporated by reference in its entirety. It should be noted, however, that the restraint systems described in the present invention do not require use of the PRT—they may be advantageously be utilized in any situation where the EDP is physically restrained by one or more staff members or other individuals.

Figure 6:
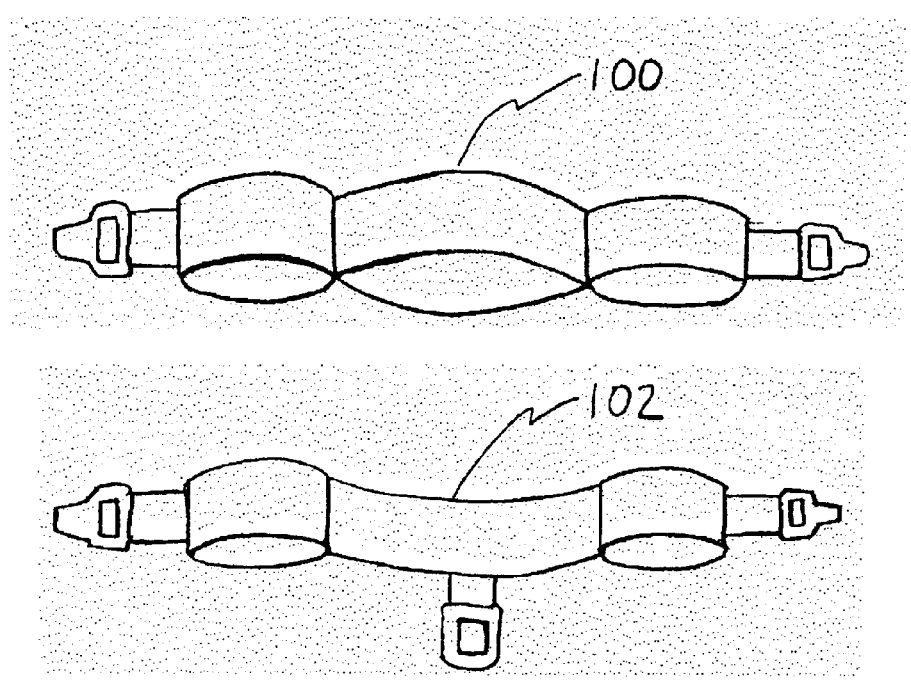
FIG. 6 shows a top isometric view of the wrist and ankle mechanical restraint system restraint connection system used in conjunction with the inventive restraint transport and deployment apparatus of FIG. 1.

Referring now to FIG. 6, a wrist restraint system 100 and an ankle restraint system 102 used in conjunction with the inventive RSTD system are shown. These may be the systems disclosed in the above-incorporated R1, or any other wrist and ankle restraint systems with optional interconnects that preferably include some form of a releasable attachment device on their surface, such as hook or loop material strips, etc. The wrist and ankle restraint systems 100, 102 are advantageously utilized to quickly and safely restrain the EDP in a controlled position.

Figure 7:
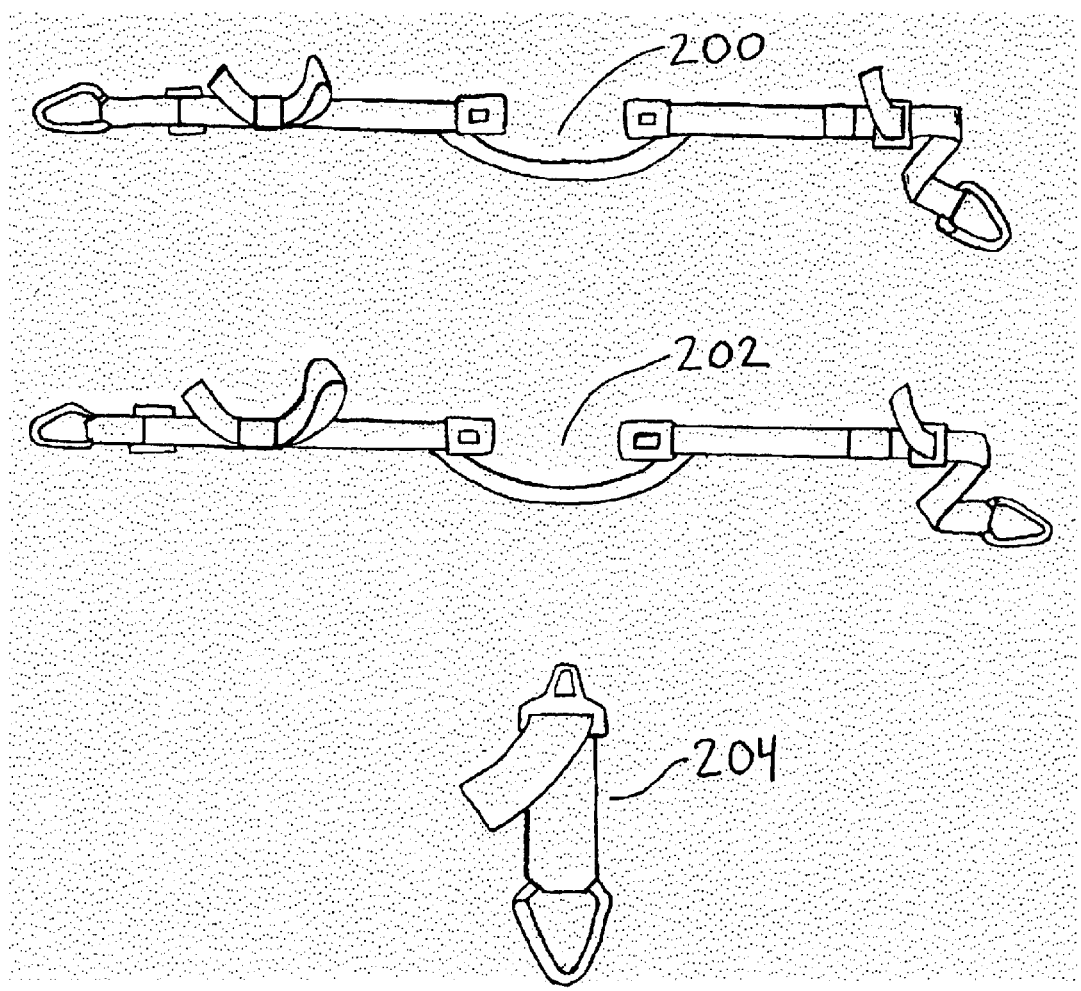
FIG. 7 shows a top isometric view of the multi-point releasable restraint connection system used in conjunction with the inventive restraint transport and deployment apparatus of FIG. 1.

Referring now to FIG. 7, a wrist point restraint connector system 200, an ankle point restraint connector system 202, and an optional ankle tensioning point connector system 204, used in conjunction with the inventive RSTD system, are shown. The connector systems 200, 202, 204 are utilized in conjunction with the wrist and ankle restraint systems 100, 102 to secure the EDP to a bed or other stationary or mobile structure. The connector systems 200, 202, 204 are preferably the ones disclosed in the above-incorporated R2, but may be any other point connector devices used to releasably connect the wrist and ankle restraints on the EDP to a stationary or mobile structure.

In summary, the RSTD system of the present invention comprises a first flexible storage platform for storing the restraint systems 100, 102, as well as supplemental restraint components used with those systems, and a removable second flexible tray for storing the multi-point connector systems 200, 202, and 204. The inventive RSTD system is stored and transported in a convenient and light rolled-up configuration. Once placed on a deployment surface, such as a bed, the RSTD system is unrolled, the second tray is removed and the first tray opened, to expose the restraint systems 100, 102 for use. The second tray is configured such that the various point connector elements are facing the portion of the bed (or similar structure) on which they must be deployed. As the point connector systems 200, 202 and 204 are pulled out of their storage compartments in the second tray, they are automatically positioned in the appropriate areas and only need to be connected to the bed or other structure in order to be fully deployed. Thus, easy and intuitive deployment is hereby achieved.

Figure 2:
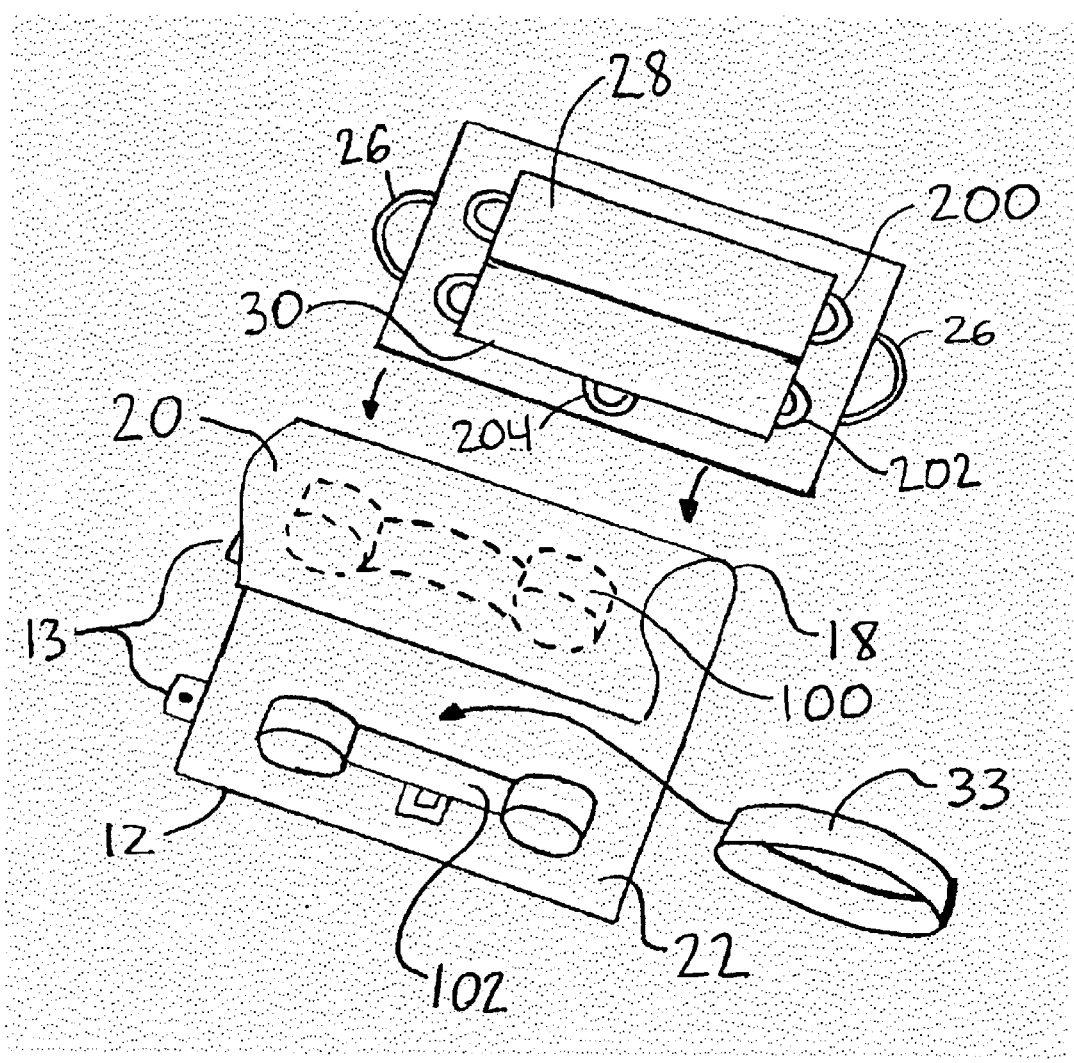
FIG. 2 shows an isometric top view of the lower tray of FIG. 1 in a partially deployed position and the upper tray of FIG. 1 in an storage configuration.
Figure 3A:
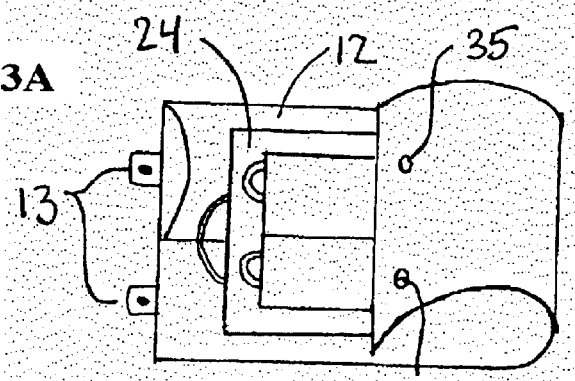
FIG. 3A shows a top isometric view of the inventive restraint transport and deployment apparatus of FIG. 1 in a partially configured storage position.
Figure 3B:
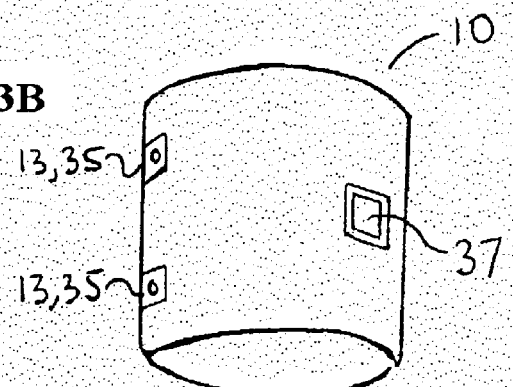
FIG. 3B shows a top isometric view of the inventive restraint transport and deployment apparatus of FIG. 1 in a storage position.

Referring now to FIGS. 1–3B, the inventive RSTD system is shown as RSTD system 10. FIG. 1 shows RSTD system 10 in a disassembled configuration ready to receive the various restraint system components, while FIG. 2 shows the RSTD system 10 is a partially assembled configuration. FIG. 3A shows the RSTD system 10 in a partial storage configuration, while FIG. 3B shows the RSTD system 10 in the final storage configuration. The RSTD system 10 includes a first tray 12 for storing the restraint systems 100, 102, and a second tray 24 for storing point connector systems 200, 202, and 204. The first and second trays 12, 24 are preferably made from a strong, thin, flexible material, such as nylon or the like.

The first tray 12 includes a first releasable connector set 14 for releasably attaching to the ankle restraint system 102, and a second releasable connector set 16 for releasably attaching to the wrist restraint system 100. The releasable connector sets 14, 16 are preferably positioned and configured to readily align with and releasably connect to corresponding releasable connectors on the respective restraint systems 100, 102 (not shown) when the restraint systems 100, 102 are placed in open positions ready for deployment. The releasable connector sets 14, 16 may be of any releasable material (i.e. hook/loop strips, button clasps, slide connectors, magnets, etc.) used in conjunction with corresponding material on the restraint systems 100, 102. For example, if the connector sets 14 and 16 are hook material, they will releasably connect to corresponding loop material areas on the restraint systems 100, 102. Optionally, when the restraint systems 100, 102 are not provided with releasable connectors, the releasable connector sets 14, 16 may be single component connectors such as releasable adhesive strips.

The second tray 24, includes substantially centrally longitudinally positioned storage flaps 28, 30, preferably composed, of a thin flexible and resilient material, such as stretchable synthetic webbing or mesh, for releasably retaining the point connector systems 200, 202, and 204 in desirable positions on the second tray 24. The storage flaps 28, 30 may be two separate components or may form a single storage cover. The lower edges of the storage flaps 28, 30 (or a central longitudinal portion, if the storage flaps 28, 30 form a single cover) are attached to the surface of the second tray 24. Optionally, the lower edges/central portion may be releasably attached to the second tray 24 so that the storage flaps 28, 30 or cover 28, 30 may be completely removed from the second tray 24.

The underside area of the storage flap 28 preferably includes a plurality of releasable connectors shown as releasable connector area 36 that match and correspond to a releasable connector area 34, having a plurality of matched releasable connectors disposed therein, on the upper surface of the second tray 24. The releasable connector areas 34 and 36 are configured and positioned such that when the point connector system 200 is placed substantially within the boundary formed by the releasable connector area 34, and the storage flap 28 is moved into contact with the second tray 24, the releasable connector areas 34 and 36 releasably engage one another and secure the point connector system 200 in a pocket formed between the storage flap 28 and the second tray 24. Preferably, as shown in FIG. 2, small portions of the stored point connector system 200 protrude from the pocket to enable a staff member to quickly remove the system 200 from the tray 24 during deployment (as described in greater detail below in connection with FIG. 5).

Similarly, the underside area of the storage flap 30 preferably includes a plurality of releasable connectors shown as releasable connector area 38 that match and correspond to a releasable connector area 32, having a plurality of matched releasable connectors disposed therein, on the upper surface of the second tray 24. The releasable connector areas 32 and 38 are configured and positioned such that when the point connector systems 202 and 204 are placed substantially within the boundary formed by the releasable connector area 32, and the storage flap 30 is moved into contact with the second tray 24, the releasable connector areas 32 and 38 releasably engage one another and secure the point connector systems 202 and 204 in a pocket formed between the storage flap 30 and the second tray 24. Preferably, as shown in FIG. 2, small portions of the stored point connector systems 202 and 204 protrude from the pocket to enable a staff member to quickly remove the systems 202, 204 from the tray 24 during deployment (as described in greater detail below in connection with FIG. 5).

The releasable connector area pairs 34, 36, and 32, 38 may be continuous releasable connectors or may each comprise a plurality of matched connection devices. For example, if the releasable connector area 34 consists of a set of hook material strips positioned at predetermined locations therein, then the releasable connector area 36 will consist of matched loop material strips positioned to align with and releasably engage with the hook material strips of the releasable connector area 34. FIG. 2 shows the second tray 24 in the storage configuration with the flaps 28 and 30 in the closed position with the point restraint systems 200, 202, 204 securely stored thereon. The second tray 24 also includes handles 26 for readily moving the tray 24 to and from the first tray 12.

Once the point restraint systems 200, 202, 204 are secured to the second tray 24 to place the RSTD system 10 into a storage configuration, the restraint systems 100, 102 are releasably connected to corresponding releasable connector sets 14, 16. Referring now to FIG. 3, a portion 20 of the first tray 12 is then folded over the stored restraint system 100, along a folding line 18, covering a part of a portion 22 of the tray 12. Optionally, a supplemental restraint system component 33, such as alternate interconnects for the wrist or ankle restraint systems 100, 102 may be then placed onto the first tray 12 between the ankle restraint system 102 and the folded portion 20, as shown in FIG. 2. The second tray 24 is then placed on top of the folded first tray 12 and the two trays 12, 24 are rolled up from one side to another as shown in FIG. 3A. A pair of releasable connectors 13 is positioned on one side of the tray portion 22 that may be secured to matching connectors 35 on the bottom surface of the tray portion 22. The releasable connectors 13, 35 are used to secure the entire RSTD system 10 into a storage/transport position when it is fully rolled up as shown in FIG. 3B. An external pocket 37 may be provided on the outer surface of the lower tray 12 for a card that may serve to log signatures of users and dates of use for record-keeping. When the RSTD system 10 is in its storage position as shown in FIG. 3B, the RSTD system 10 is easy to store and transport.

Figure 4:
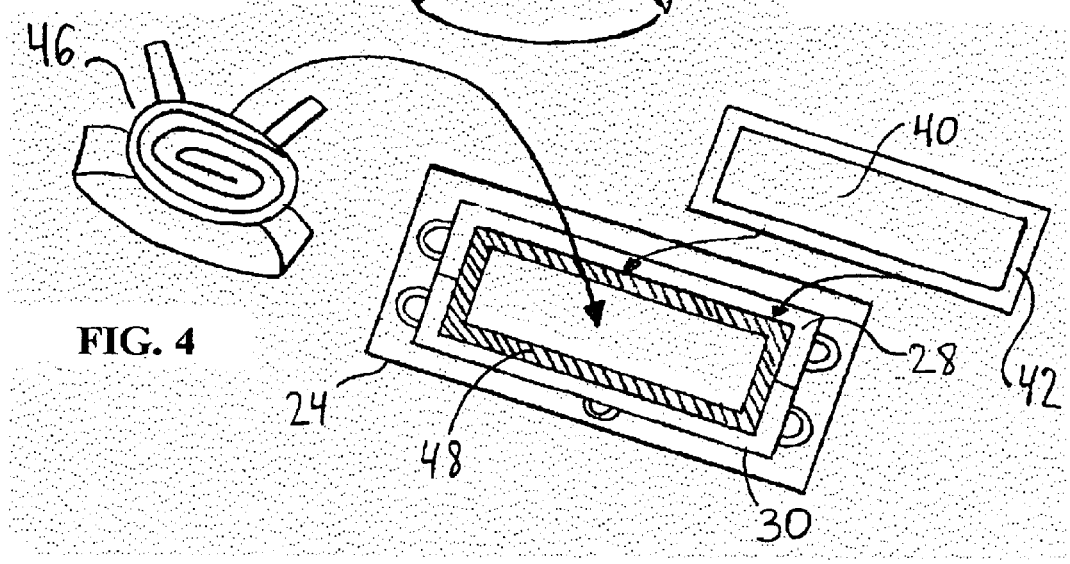
FIG. 4 shows a top isometric view of the an alternate embodiment of the top tray of FIG. 1 which includes a top-mounted storage compartment for storing an articulated upper body protection restraint system.

Referring now to FIG. 4, in an alternate embodiment of the second tray 24, an optional secondary restraint storage compartment, for storing a supplemental restraint system 46 is provided by a removable cover 40 releasably mounted on the upper surfaces of the flaps 28, 30 of the second tray 24. The underside area of the cover 40 preferably includes a plurality of releasable connectors shown as releasable connector area 42 that match and correspond to a releasable connector area 48, having a plurality of matched releasable connectors disposed therein, on the upper surface of the flaps 28, 30. The releasable connector areas 42 and 48 are configured and positioned such that when the a supplemental restraint system 46 is placed substantially within the boundary formed by the releasable connector area 48, and the cover 40 is moved into contact with the flaps 28, 30, the releasable connector areas 42 and 48 releasably engage one another and secure the a supplemental restraint system 46 in a pocket formed between the cover 40 and the flaps 28, 30. The cover 40 preferably consists of a flexible and resilient material that is capable of stretching to accommodate the supplemental restraint system 46 in a relatively small storage area.

The releasable connector areas 42, 48 may be continuous releasable connectors or may each comprise a plurality of matched connection devices. For example, if the releasable connector area 42 consists of a set of hook material strips positioned at predetermined locations therein, then the releasable connector area 48 will consist of matched loop material strips positioned to align with and releasably engage with the hook material strips of the releasable connector area 42. The supplemental restraint system 46 may be any additional restraint system, such as a the system disclosed in the above-incorporated commonly assigned co-pending U.S. provisional patent application entitled "Articulated Upper Body Protector Restraint Apparatus and Method".

Preferably, small portions of the stored supplemental restraint system 46 protrude from the pocket to enable a staff member to quickly remove the system 46 from its stored position during deployment (as described in greater detail below in connection with FIG. 5). The additional storage compartment formed by the cover 40 and the releasable connector areas 42, 48 do not affect the storage configuration of the RSTD system 10 which may be still be rolled up and secured for storage/transport as shown in FIG. 3B.

Figure 5:
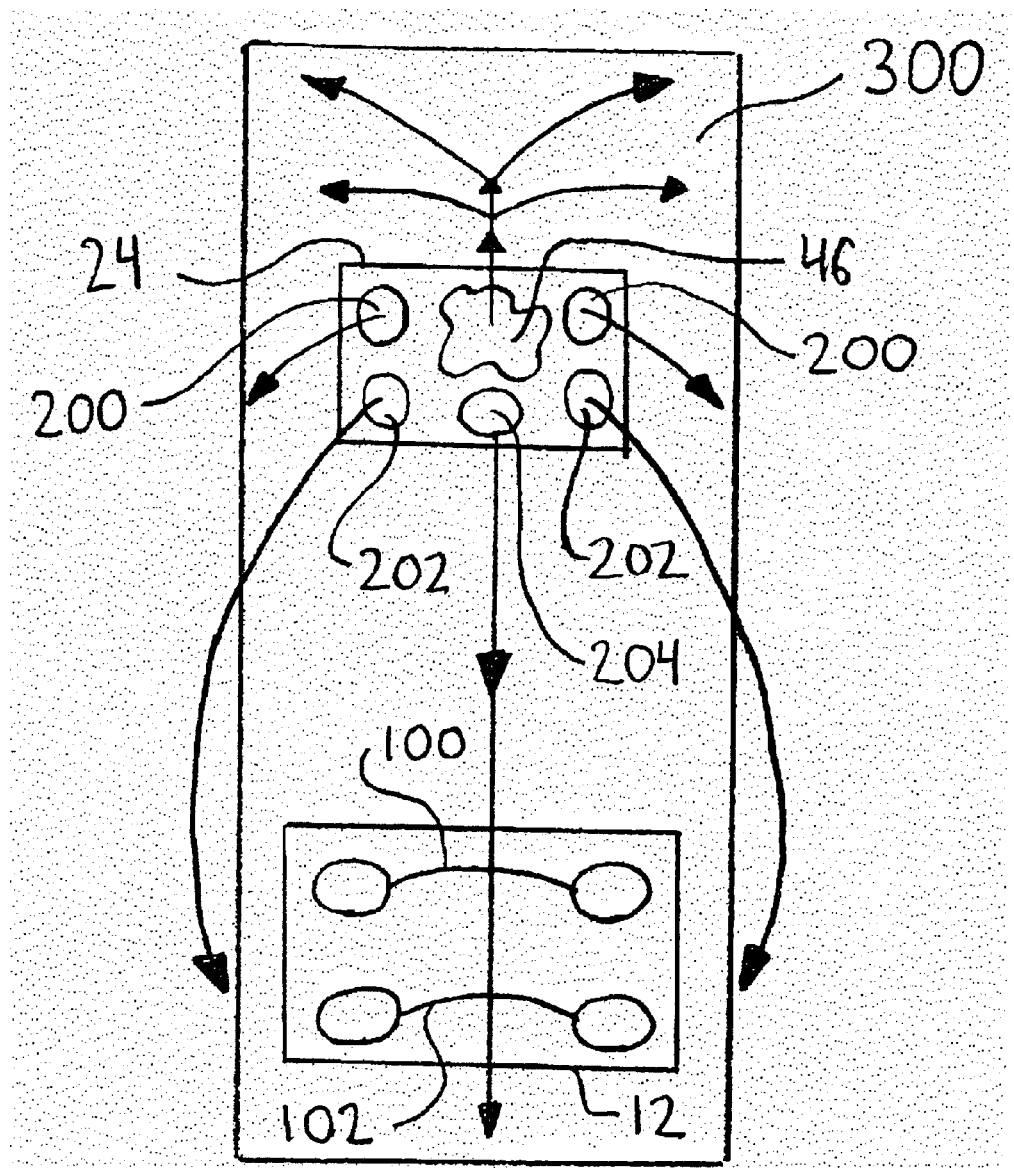
FIG. 5 is a schematic diagram showing rapid deployment of various restraint systems from the inventive restraint transport and deployment apparatus of FIG. 1 onto a bed.

Referring now to FIG. 5, exemplary advantageous rapid deployment aspect of the inventive RSTD system 10 on a bed 300 is shown. The RSTD system 10 is placed on the bottom portion of the bed 300 and unrolled such that the ankle restraints face the bottom of the bed 320. The second tray 24 is then removed and placed above the first tray 12. A staff member is free to remove the wrist and ankle restraint systems 100, 102, for application to the EDP, from the first tray 12 while they (or another) prepares the point connector systems 200, 202, 204 and the optional supplemental restraint system 46.

The staff member then grasps the protruding portions of the supplemental restraint system 46 and pulls upward to automatically disengage the releasable connector areas 42, 48 and remove the system 46 from beneath the cover 40, and then move it into the top portion of the bed 300 where it may be prepared to receive the EDP.

The staff member then grasps the protruding portions of the point connector system 200 and pulls to the sides and upward to automatically disengage the releasable connector areas 34, 36 and remove the system 200 from beneath the flap 28, and then move it into the middle portion of the bed 300 where it may be connected to the bed 300 and prepared to receive the EDP. The process is repeated with the connector systems 202, 204 as shown in FIG. 5. As a result, the various restraint components 46, 100, 102, 200, 202, and 204 may be quickly and intuitively deployed from the RSTD system 10 by a single staff member and be ready to secure the restrained EDP to a mobile or stationary structure in less than a minute.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

I claim:

1. An apparatus for storing, transporting, and deploying mechanical wrist and ankle restraint systems for restraining a person, a plurality of restraint point connection systems for connecting the wrist and ankle restraints to a structure, the apparatus comprising:

a rectangular flexible first tray having an upper and lower surface, sized and configured to receive the wrist and ankle restraint systems, comprising a first section on said upper surface of said first tray for positioning the wrist and ankle restraint systems thereon, and a first flap operable to fold over at least a portion of said first section;

a first releasable connection means, positioned in said first section, for releasably connecting the wrist and ankle restraint systems thereto; and a rectangular flexible second tray, sized smaller than said first tray, having an upper surface comprising a plurality of compartments for receiving the plural restraint point connector systems, each said plural compartment further comprising a second releasable connection means for releasably securing at least a portion of the plural restraint point connector systems within each said compartment, wherein:

(1) in a storage configuration, said second tray is positioned on top of said first tray after said first flap has been folded, and said first and second trays are rolled from one side to another into a generally cylindrical shape, and (2) in a deployment configuration, said first and second trays are unrolled from said storage configuration, said second tray is removed from said first tray and the wrist and ankle restraint systems and the plural restraint point connection systems are removed therefrom by disengaging said first releasable connection means and said plural second releasable connection means, respectively.

2. The apparatus of claim 1, further comprising a releasable secondary storage compartment positioned on said plural storage compartments for receiving and storing an additional supplemental restraint system, said releasable secondary storage compartment further comprising a third releasable connection means for releasably retaining the additional supplemental restraint system within said releasable secondary storage compartment.

3. The apparatus of claim 1, wherein said first and second trays are composed from thin flexible synthetic materials having high tensile strength.

4. The apparatus of claim 1, wherein said first releasable connection means comprises at least one set of hook or loop material strips configured to releasably attach to portions of the wrist and ankle restraint systems, and wherein each of said plural second releasable connection means comprises a first set of at least one hook and loop material strips and a second set of at least one hook and loop material strips, wherein first set of at least one hook and loop material strips is positioned on said upper surface of said second tray and configured to releasably connect to said second set of at least one hook and loop material strips positioned on an upper portion of each said plural compartment.

5. The apparatus of claim 1, wherein said plural compartments comprise at least one rectangular flexible cover placed over said upper surface of said second tray and releasably secured thereto by said plural second releasable connection means.

6. The apparatus of claim 1, wherein said second tray comprises a pair of side handles to facilitate moving said second tray to and from said first tray.

7. The apparatus of claim 1, further comprising fourth releasable connection means for releasably securing said first and second trays in said storage configuration.

8. The apparatus of claim 1, wherein said first tray further comprises an lower surface, further comprising a compartment positioned on said lower surface for receiving an insert having apparatus usage, time, and user identification data imprinted thereon.

9. A method of storing, transporting, and deploying mechanical wrist and ankle restraint systems for restraining a person, a plurality of restraint point connection systems for connecting the wrist and ankle restraints to a structure, the method comprising the steps of:
  (a) providing a flexible first tray having an upper and lower surface, sized and configured to receive the wrist and ankle restraint systems, comprising a first section on said upper surface of said first tray for positioning the wrist and ankle restraint systems thereon, and a first flap operable to fold over at least a portion of said first section;
  (b) releasably connecting the wrist and ankle restraint systems to said first section and closing said first flap over at least a portion of said closed section;
  (c) providing a flexible second tray, sized smaller than said first tray, having an upper surface comprising a plurality of releasably closing compartments for receiving the plural restraint point connector systems;
  (d) placing the plural restraint point connector systems into said plural releasably closing compartments;
  (e) positioning said second tray on top of said first tray;
  (f) rolling said first and second trays said first and second trays from one side to another into a generally cylindrical shape; and
  (g) when deployment of the wrist and ankle restraint systems and said plural restraint point connection systems is desirable:
    (1) unrolling said first and second trays
    (2) removing said second tray from said first tray
    (3) removing the plural restraint point connector systems from said second tray for releasable connection to the structure; and
    (4) removing the wrist and ankle restraint systems from said first tray for application to the subject.

10. The method of claim 9, wherein said step (d) further comprises placing the plural restraint point connector systems into said plural releasably closing compartments such that at least a portion of each plural point connector system is accessible from outside said plural releasably closing compartments, and wherein said step (g)(3) further comprises the steps of:
  (h) pulling each of said plural portions with sufficient force to disengage said plural releasably closing compartments; and
  (i) positioning each plural point connector system on the structure, in predetermined positions matching functionality of each plural point connector system, to facilitate connection thereto.

11. The method of claim 9, wherein the structure is a bed having a head portion, a central portion, and a foot portion, wherein said step (g) (2) further comprises positioning said first tray proximal to the foot portion and positioning said second tray at said central portion.

* * * * *